United States Patent [19]

Valdes

[11] 4,057,403
[45] Nov. 8, 1977

[54] GAS TREATING PROCESS

[75] Inventor: A. R. Valdes, Houston, Tex.

[73] Assignee: Fluor Corporation, Los Angeles, Calif.

[21] Appl. No.: 410,626

[22] Filed: Oct. 29, 1973

[51] Int. Cl.$^2$ .............................................. B01D 53/14
[52] U.S. Cl. ............................................ 55/31; 55/73
[58] Field of Search ...................................... 55/29–32, 55/171–177, 73; 423/228

[56] References Cited

U.S. PATENT DOCUMENTS

| 2,712,978 | 7/1955 | Blohm et al. | 423/228 |
| 3,531,915 | 10/1970 | Nagel et al. | 55/32 |

Primary Examiner—John Adee
Attorney, Agent, or Firm—Cushman, Darby & Cushman

[57] ABSTRACT

Gaseous hydrocarbon streams such as natural gas streams are acid gas depleted and reduced to pipeline specification moisture content using a single absorbent: a particular amino ethyl ether; in two steps providing in sequence, counter-current multi-stage absorption and at least one dehydrating contact stage with fresh absorbent at low temperature, to effect moisture removal down to 4 pounds of water per MMSCF of gas and even lower water content. The use of a single chemical as absorbent rather than two absorbents means lower capital investment and operating expense than heretofore required to get pipeline specification gas.

12 Claims, 1 Drawing Figure

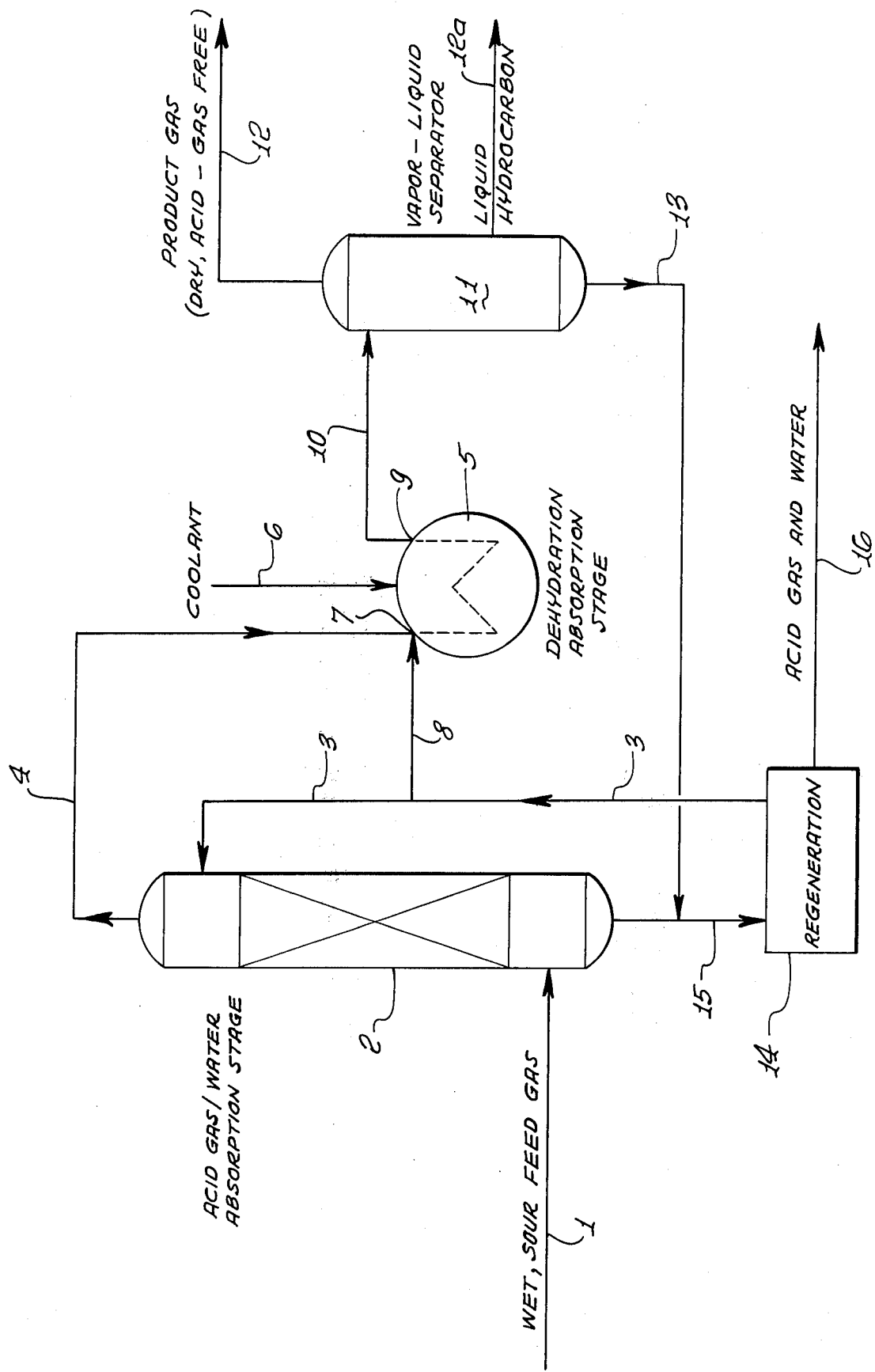

GAS TREATING PROCESS

BACKGROUND OF THE INVENTION

This invention has to do with treating gaseous hydrocarbon streams to have pipeline specifications. Among such specifications are substantial absence of acid gas, e.g. carbon dioxide and hydrogen sulfide, and as well very low moisture contents, now typically as low as 4–7 pounds and less of water per million standard cubic feet (MMSCF) of gas.

PRIOR ART

Numerous agents have been proposed to remove acid gases from hydrocarbons. Numerous other agents have been proposed to remove moisture contents from gaseous hydrocarbons. In U.S. Pat. No. 2,712,978 to Blohm et al, a single absorbent, an hydroxy amino ether, is disclosed to function as both an acid gas remover and a dehydrator. In practice these hydroxy amino ethers have been used to remove acid gas and moisture, but the moisture removal has been insufficient to obtain pipeline specification gas. Accordingly, it has been the practice to follow the hydroxy amino ether treatment of the gas with a glycol dehydration step.

Glycol dehydration is used in conventional treatment of gas to pipeline specification by mixing the gas with a glycol such as ethylene glycol, diethylene glycol or triethylene glycol and indirectly cooling the mixture, it having been found that at a given temperature for the cooled mixture, substantially more moisture is condensed from the gas stream with the glycol present than without the glycol. Generally glycol treatment follows an acid gas removal step, which conventionally has been selective absorption of acid gases, e.g. an aqueous solutions of ethanolamines or of potassium carbonate, which effectively remove the acid gases but do not remove substantial amounts of moisture.

Obviously, circulating and regenerating different solvents as separate absorbents, one for acid gases and one for moisture requires double piping and storage systems and added investment and operating expense.

Thus the discovery of certain hydroxy amino ethers, described in the aforementioned U.S. Pat. No. 2,712,978, which per se and in aqueous solution both absorb acid gases and remove moisture was an important breakthrough. Nonetheless the use of hydroxy amino ethers as described in this patent does not bring the gas to pipeline specifications and accordingly a separate treatment with a different solvent, e.g. alkylene glycol, was still required where pipeline specification gas was needed.

Thus the single absorbent idea was not realized and double piping, storage and regeneration facilities were continued to be used.

SUMMARY OF THE INVENTION

It has now been surprisingly discovered that a two stage treatment with the single absorbent, hydroxy amino ether, effectively removes moisture down to pipeline specifications, i.e. 4–7 pounds of water per MMSCF; or even substantially less; the first stage comprising gas-liquid absorption of acid gas and moisture vapor by the absorbent, and the second stage comprising mixing treated gas from the first stage with fresh absorbent, and cooling the mixture, whereby some remaining acid gas and most of the residual water is absorbed by the solvent.

The present method thus provides the objective of a single absorbent, in a plant capable of producing pipeline specification gas. Other objects of single storage facilities, reduced piping, and common regeneration operations are also realized, resulting in lower cost operations, and reduced capital expense.

In particular, the invention provides in the process of treating a gaseous hydrocarbon stream for the removal therefrom of hydrogen sulfide, carbon dioxide or both acid gases, and moisture, by intimately contacting the stream with a lean absorbent, the absorbent comprising an hydroxy amino ether having the general formula

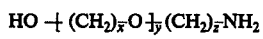

wherein
$x = 2$ or $3$
$y = 1, 2, 3,$ or $4$
$z = 2$ or $3$, and gas-liquid absorbing the acid gas and a first quantity of moisture in the vapor phase in the absorbent, separating the acid-gas rich, moisture-containing absorbent, and regenerating the absorbent with heat in a first stage, the improvement comprising in a second stage, dispersing dehydrating agent comprising additional lean absorbent in the hydrocarbon stream obtained from the first stage, cooling the absorbent-hydrocarbon stream mixture to condense the residual moisture therein into solution with the absorbent, thereby absorbing the condensed residual moisture in the lean absorbent separating a product gas having a moisture content of not more than 7, and generally 4 or fewer pounds of water per MMSCF; and regenerating the absorbent with heat.

Advantageously, the moisture containing absorbent from both the first and second stages may be combined for regeneration with common heating.

Typically the absorbent is an aqueous solution of the hydroxy amino ether, and preferably comprises 60% and most preferably 70% by weight and higher, up to 75% of the hydroxy amino ether. Also typically the hydrocarbon stream in the second stage after absorbent dispersal therein, is cooled to below ambient temperatures, e.g. to below 10° F. Dispersal of the absorbent into the hydrocarbon stream is readily accomplished by spraying the absorbent into the gas stream, suitably into the heat exchanger inlet.

Two especially preferred hydroxy amino ethers are $\beta,\beta'$-hydroxy amino ethyl ether and $\beta$-hydroxy ($\beta$-amino ethoxy) ethyl ether.

BRIEF DESCRIPTION OF THE DRAWINGS

The invention will be further described as to an illustrative embodiment in conjunction with the attached drawing in which a flow sheet depiction of the process is given in the single FIGURE.

DESCRIPTION OF THE PREFERRED EMBODIMENTS

The specification, description and drawing of U.S. Pat. No. 2,712,978 to Blohm is incorporated herein by reference.

Referring now to the drawing a feed gas in line 1 comprising raw natural gas at a temperature above about 80° F and containing substantial amounts of moisture, i.e. water in the vapor state, e.g. typically between 30 and 80 pounds per MMSCF and also substantial amounts of acid gases, either or both of hydrogen sulfide and carbon dioxide, e.g. typically between 5 and 20% by weight of these, is introduced near the bottom to a first absorber shown as a countercurrent contact tower absorber 2. Lean absorbent containing from 25 to 40% by weight water and preferably comprising $\beta,\beta'$ hydroxy amino ethyl ether or a mixture thereof with another hydroxy amino ether, in solution, at a temperature between 90° and 120° F from the regeneration unit to be described, is introduced near the top of the tower 2 through line 3. In this manner ascending gas in the tower 2 is contacted usually enhanced by column packing or gas-liquid contact trays, e.g. bubble cup or valve trays, of conventional design. As a result of this intimate contact of the aborbent and the acid gases in the hydrocarbon, the bulk of the acid gases is transferred from the hydrocarbon and absorbed in the absorbent, by reaction or solution therein. This reaction or solution is exothermic, effecting a warming of the liquid in the absorber 2 as it descends. The gas in the absorber 2 having substantially less heat capacity than the liquid absorbent, rises to leave the absorber, through line 4, and at a temperature approximating the incoming lean absorbent temperature, typically between 90° and 120° F and preferably between 100° and 110° F. As noted above, and in the aforementioned U.S. Pat. No. 2,712,978, the moisture content of the hydrocarbon is reduced along with the acid gas content using the described hydroxy amino ethers. Typically the water content of the feed may be reduced from 65 pounds per MMSCF to 54 pounds in the exit gas in line 4, a substantial improvement but excessive for pipeline specification gas, by the just described step.

In the past, the gas in line 4 has been further treated with glycol, as mentioned above, to pipeline specifications, although this necessitated additional and separate piping, storage and regeneration equipment.

In accordance with the present invention, however, and in a departure from past practice, additional fresh lean hydroxy amino ether absorbent is dispersed into the hydrocarbon gas. Thus the hydrocarbon gas in line 4 is passed to heat exchanger 5, cooled with coolant in line 6, to lower the temperature of the hydrocarbon gas to less than ambient, i.e. to 10° F or lower. At the inlet 7 of heat exchanger 5, line 8 introduces lean hydroxy amino ether from line 3 and regeneration unit 14. The introduction may be by spraying directly into the gas in inlet channel of the heat exchanger or the spray may be onto the inlet tube sheet, in either case the spray is provided in a manner to disperse the hydroxy amino ether intimately in droplet form through the gas stream. Thus intimately interdispersed with the absorbent, the gas is cooled in the heat exchanger 5. Generally the gas temperature is lowered from 110° F which is the temperature at the exit of absorber 2 to 0° F or lower at the outlet 9 of the heat exchanger 5 where the cooled gas exits, aided by the presence of the absorbent. Within heat exchanger 5, the gas which is at a pressure between about 900 and 950 psig yields water condensate which dissolves in the liquid absorbent, in the dehydration-absorption stage of the process. The gas, and water-enriched absorbent, is passed from the heat exchanger outlet 9 along line 10 to vapor-liquid separator 11. There the product, pipeline specification natural gas, exits through line 12, liquid hydrocarbon exits through line 12a, while the liquid absorbent and its water content are passed along line 13 to the regeneration unit 14 via line 15 which carries the water-rich and acid gas-rich absorbent from gas-liquid absorber 2. Within the regeneration unit, the absorbent is regenerated with heat and the lean absorbent passed back to the first and second stages, through line 3 and line 8 respectively for reuse. Acid gases and water are passed to water through line 16.

EXAMPLE 18,000 pound moles per hour of a feed gas of the following composition

| | |
|---|---|
| $CH_4$ | 84.65 |
| $C_2H_6$ | 7.21 |
| $C_3H_8$ | 1.27 |
| $N_2$ | .44 |
| $iC_4$ | .14 |
| $nC_4$ | .19 |
| $iC_5$ | .07 |
| $nC_5$ | .07 |
| $C_6^+$ | .26 |
| $H_2S$ | .43 |
| $CO_2$ | 5.27 |
| $H_2O$ | saturated | at temperature of 100° F and a pressure of 945 psig is charged to a counter-current absorber with an internal diameter of 96 inches. The absorber contains 20 valve trays. 1050 gpm of lean aqueous solution of $\beta,\beta'$ hydroxy amino ethyl ether containing 70% by weight of ether containing only a trace of $H_2S$ and $CO_2$ ($<$ 3 wt. %) is flowed counter-currently downward through the absorber. The temperature of the solution is 110° F and the pressure is about 100 psi above the operating pressure of the absorber. Rich absorbent solution comprising the lean solution and absorbed $CO_2$, $H_2S$, and $H_2O$ flows out of the bottom of the absorber at 196° F.

Overhead gas from the absorber is at 110° F and has the following composition:

| | |
|---|---|
| $CH_4$ | 89.74 |
| $C_2H_6$ | 7.66 |
| $C_3H_8$ | 1.34 |
| $N_2$ | .47 |
| $iC_4$ | .15 |
| $nC_4$ | .21 |
| $iC_5$ | .08 |
| $nC_5$ | .08 |
| $C_6^+$ | .27 |
| $H_2S$ | trace |
| $CO_2$ | trace |
| $H_2O$ | 54#/MMSCF |

As the gas enters a refrigerated heat exchanger, 7 gpm of the aforesaid aqueous solution of $\beta,\beta'$ hydroxy amino ethyl ether is sprayed into the exchanger inlet. In the exchanger the mixture is cooled to 0° F whereupon water condenses into solution in the absorbent and is passed to a vapor-liquid separator.

The separated gas has the following composition:

| | |
|---|---|
| $CH_4$ | 90.29 |
| $C_2H_6$ | 7.55 |
| $C_3H_8$ | 1.26 |
| $N_2$ | .47 |
| $iC_4$ | .13 |
| $nC_4$ | .17 |
| $iC_5$ | .05 |
| $nC_5$ | .05 |
| $C_6^+$ | .03 |
| $H_2S$ | .09 gr/100 scf |
| $CO_2$ | trace |
| $H_2O$ | 1.4 #/MMSCF |

The separated liquid which contains in solution the moisture removed from the gas stream in the heat exchanger and also a small amount of additional $CO_2$ and $H_2S$ which was removed during the dehydration is combined with the rich solution from the absorber. The mixed solutions are passed to the regeneration unit where they are heated to 230° F and charged to a stripper which is 78 and 120 inches in inside diameter for top and bottom sections respectively. The stripper contains 20 valve trays. The temperature in the bottom of the stripper is maintained at 278° F by a stream heated reboiler. The overhead vapor from the stripper is passed through a condenser to which aqueous absorbent is condensed and used as reflux to the stripper. The uncondensed portion of the overhead contains the net $CO_2$, $H_2S$, and $H_2O$. The bottom liquid from the stripper is regenerated and lean aqueous absorbent which is cooled and used both as lean solvent for acid gases and as dehydrating agent as previously described.

The hydroxy amino ethers useful herein are those described in U.S. Pat. No. 2,712,978. That is, useful are those hydroxy amino alkyl ethers having the formula

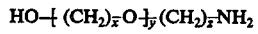

in which X is an integer from 2 to 3 inclusive, $y$ is an integer from 1 to 4 inclusive and z is an integer from 2 to 3 inclusive. Specifically preferred are $\beta,\beta'$-hydroxy amino ethyl ether:

and $\beta$-hydroxy ($\beta'$-amino ethoxy) ethyl ether:

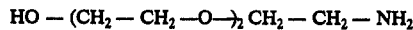

I claim:

1. In the process of treating a gaseous hydrocarbon stream for the removal therefrom of hydrogen sulfide, carbon dioxide or both acid gases, and moisture, by intimately contacting the stream with a lean absorbent, said absorbent comprising an hydroxy amino ether having the general formula

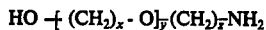

wherein $x$ is 2 or 3, $y$ is 1 to 4 and $z$ is 2 or 3, and gas-liquid absorbing the acid gas and a first quantity of vapor phase moisture in said absorbent, separating the acid gas-rich, moisture-containing absorbent and regenerating the absorbent with heat in a first stage; the improvement comprising in a second stage dispersing a dehydrating agent comprising additional lean absorbent in the hydrocarbon stream obtained from the first stage, cooling the absorbent-hydrocarbon stream mixture to condense residual moisture therein into solution in the absorbent separating a product gas having a moisture content of not more than 7 pounds of water per MMSCF; and regenerating the absorbent with heat.

2. The process according to claim 1 including also combining the moisture-containing absorbents from the first and second stages for regeneration with common heating.

3. The process according to claim 1 in which said absorbent comprises an aqueous solution containing 60 to 75% of said hydroxy amino ether.

4. The process according to claim 3 in which said aqueous absorbent solution comprises 70% by weight hydroxy amino ether.

5. The process according to claim 1 including also cooling the hydrocarbon stream in the second stage below ambient temperature.

6. The process according to claim 1 in which said hydroxy amino ether is $\beta,\beta'$-hydroxy amino ethyl ether.

7. The process according to claim 1 in which said hydroxy amino ether is $\beta'$-hydroxy ($\beta$-amino ethoxy) ethyl ether.

8. In the process of treating a gaseous hydrocarbon stream for the removal therefrom of hydrogen sulfide, carbon dioxide or both, and moisture, by intimately contacting the stream with a lean absorbent, comprising $\beta$, $\beta'$-hydroxy amino ethyl ether or $\beta'$-hydroxy ($\beta$-amino ethoxy) ethyl ether, and absorbing the acid gas and the first quantity of vapor phase moisture in said absorbent and separating the acid gas-rich, moisture-containing absorbent from the hydrocarbon stream in a first stage, the improvement comprising in a second stage spraying dehydrating agent comprising additional lean absorbent as a 60 to 75% aqueous solution into the hydrocarbon stream obtained from the first stage, cooling the absorbent-hydrocarbon stream mixture to condense residual moisture therein into solution in the absorbent, combining the absorbents of the first and second stages, heat regenerating said absorbents together, and separating a product gas having a content of not more than 4 pounds of water per MMSCF.

9. The process claimed in claim 8 in which the second stage absorbent is sprayed into the cooling heat exchanger inlet.

10. The process claimed in claim 8 in which the second stage absorbent-hydrocarbon stream mixture is cooled to less than ambient temperature.

11. The process according to claim 10 in which the absorbent is $\beta$, $\beta'$-hydroxy amino ethyl ether.

12. The process according to claim 10 in which the absorbent is $\beta'$-hydroxy ($\beta$-amino ethoxy) ethyl ether.

* * * * *